US009702830B1

(12) United States Patent
Akselrod et al.

(10) Patent No.: US 9,702,830 B1
(45) Date of Patent: *Jul. 11, 2017

(54) PAVEMENT MARKING DETERMINATION (71) Applicant: International Business Machines Corporation, Armonk, NY (US)

(72) Inventors: Ben Z. Akselrod, Givat Shmuel (IL); Anthony Di Loreto, Markham (CA); Steve McDuff, Markham (CA); Kyle D. Robeson, North York (CA)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/099,264

(22) Filed: Apr. 14, 2016

Related U.S. Application Data (63) Continuation of application No. 15/004,170, filed on Jan. 22, 2016.

(51) Int. Cl.
*G06K 9/58* (2006.01)
*G01N 21/956* (2006.01)
(Continued)

(52) U.S. Cl.
CPC ... *G01N 21/95607* (2013.01); *G06K 9/00798* (2013.01); *G06T 7/0004* (2013.01); *H04L 67/12* (2013.01); *B60R 11/04* (2013.01)

(58) Field of Classification Search
None
See application file for complete search history.

(56) References Cited

U.S. PATENT DOCUMENTS 3,101,175 A 8/1963 Brown, Jr.
5,203,923 A 4/1993 Hartman
(Continued)

FOREIGN PATENT DOCUMENTS

CN 103498411 A 1/2014

OTHER PUBLICATIONS

Ali et al., "Autonomous Mobile Robotic System for On-the-Road Painting", Proceedings of the 14th International Conference on Robotics, Control and Manufacturing Technology (ROCOM '14), Kuala Lumpur, Malaysia, Apr. 23-25, 2014, pp. 98-103, <www.wseas.org/main/books/2014/Malaysia/ROCOM.pdf>.
(Continued)

*Primary Examiner* — Nicholas Kiswanto
*Assistant Examiner* — Kyung Kim
(74) *Attorney, Agent, or Firm* — Maeve Carpenter (57) ABSTRACT In an approach to determining pavement markings, a computer determines a location of a first computing device based on data received from one or more location devices associated with the first computing device. The computer then retrieves pavement marking data for one or more pavement markings for the location and determines whether one or more existing pavement markings are present at the location. Responsive to determining that one or more existing pavement markings are present at the location, the computer determines whether each of the one or more existing pavement markings meet one or more pre-determined thresholds for an acceptable pavement marking quality. Furthermore, responsive to determining each of the one or more existing pavement markings do not meet the one or more pre-determined thresholds for an acceptable pavement marking quality level, the computer provides pavement marking data to the first computing device.

1 Claim, 3 Drawing Sheets

(51) Int. Cl.
*H04L 29/08* (2006.01)
*G06K 9/00* (2006.01)
*G06T 7/00* (2017.01)
*B60R 11/04* (2006.01)

(56) References Cited

U.S. PATENT DOCUMENTS

| | | |
|---|---|---|
| 5,296,256 A | 3/1994 | Hartman |
| 5,599,133 A | 2/1997 | Costello et al. |
| 6,206,610 B1 | 3/2001 | Neuling |
| 6,299,934 B1 | 10/2001 | Manning |
| 8,224,031 B2 | 7/2012 | Saito |
| 8,467,968 B1 | 6/2013 | Dolinar et al. |
| 8,935,057 B2 | 1/2015 | Dolinar et al. |
| 2013/0184938 A1 | 7/2013 | Dolinar et al. |
| 2013/0190981 A1* | 7/2013 | Dolinar .................. B60R 11/04 701/41 |
| 2015/0127233 A1 | 5/2015 | Drennen et al. |

OTHER PUBLICATIONS

U.S. Appl. No. 15/004,170, filed Jan. 22, 2016.
List of IBM Patents or Patent Applications Treated as Related (Appendix P), filed herewith.

* cited by examiner

PAVEMENT MARKING DETERMINATION

BACKGROUND

The present invention relates generally to roadway management, and more particularly, to computers using sensors such as location sensors, depth sensors, and cameras to evaluate road pavement markings at a location and output pavement marking data for the location to a pavement painting system.

Current methods to apply pavement markings for roadways include determining a center of a road using a manual measurement of the road width. A road width may be manually measured and the center of the road is determined and marked at multiple locations along the road. Once the center of a road is determined, a truck with painting equipment uses the manually applied marks to position the truck and to guide the painting system to apply the pavement marks. The painting system is typically on a movable arm positioned by a second operator for paint application on a road surface.

Typically, the location of pavement marks for roadways such as slow lanes are manually determined using the center of a road as a reference mark for the application of pavement markings. The center of the road is used to offset additional pavement markings such as lines depicting merge lanes, bike lanes, intersection stop lines, turn arrows, etc. The pavement markings for a road are typically included in a road plan based on the required traffic control marks as defined in a manual or document for a governing entity (e.g., a providence, a state, or a country). The pavement markings can be specified in a traffic specification or document for governing traffic regulations such as a Manual on Uniform Traffic Control Devices (MUTCD) in the United States or other similar document in another country.

Existing pavement markings may be inspected or evaluated to determine if the pavement marking meet a required quality level (e.g., the pavement marks meet defined criteria or thresholds for visibility). An inspector, typically a Department of Transportation inspector or other similar trained individual, performs the inspection to evaluate if the existing pavement markings are acceptable based on one or more criteria defined in the governing traffic specifications such as the MUTCD.

SUMMARY

Aspects of the present invention provide a method, computer program product, and a computer system for one or more computers to determine determining pavement markings. The method includes determining, by one or more computers, a location of a first computing device based on data received from one or more location devices associated with the first computing device, wherein at least one of the one or more location devices includes a precision global positioning system and wherein the first computing device is one of: a mobile computing device held by an operator of a pavement painting system, a computer integrated into the pavement painting system, and an automated robotic painting system that is one of an autonomous car, an autonomous kart, or an autonomous drone. The method includes retrieving, by one or more computers, pavement marking data for one or more pavement markings for the location, and determining whether one or more existing pavement markings are present at the location, wherein the determining includes determining, based, at least in part, on at least one of: a digital image received from one or more cameras and sensor data received from one or more sensors. Responsive to determining that one or more existing pavement markings are present at the location, the method includes determining, by one or more computers, whether each of the one or more existing pavement markings meet one or more pre-determined thresholds for an acceptable pavement marking quality, wherein the one or more pre-determined thresholds for the acceptable pavement marking quality level include at least one of: a level of contrast between a pavement marking color and a pavement color, a percent of a pavement marking present, a location of a pavement marking as compared to a specified pavement mark for the location of an existing pavement marking, and any other threshold of the one or more pre-determined thresholds for an acceptable quality level included in a governing traffic regulation document. The method then includes, responsive to determining each of the one or more existing pavement markings do not meet the one or more pre-determined thresholds for an acceptable pavement marking quality level, providing, by one or more computers, pavement marking data to the first computing device, wherein providing pavement marking data includes providing data for removal of one or more of the one or more existing pavement markings and providing pavement marking data for display using augmented reality.

DETAILED DESCRIPTION

Embodiments of the present invention recognize that in road construction and road maintenance projects pavement markings of various shapes and sizes for traffic lanes, passing lines, turn arrows, and other road markings are applied. Embodiments of the present invention recognize that the method to determine a location for pavement marking application and a method of pavement marking application typically rely on predominately manual methods to determine the pavement marking location and the specified pavement markings for application prior to painting the road pavement markings. Additionally, embodiments of the present invention recognize the pavement markings for roads are periodically re-applied, in some cases, based on a manual visual inspection and evaluation of existing pavement markings.

Embodiments of the present invention provide a method, a system, and a computer program to determine if a paved area such as a new or re-surfaced road needs an initial pavement marking application. Additionally, embodiments of the present invention provide a method, a system, and a computer program for an automatic evaluation of existing pavement markings to determine if a re-painting of the existing pavement markings is needed. Embodiments of the present invention provide a method to determine when, where, and which pavement markings need to be applied using a combination of various sensors, cameras, a road plan, and at least one software program. Furthermore, embodiments of the present invention provide pavement marking data to a display that uses augmented reality to depict pavement markings on an overlay of the real-time view of the road. Additionally, embodiments of the present invention include the ability to use an automated robotic vehicle or drone to provide an evaluation, a location, pavement marking data, and an ability to paint pavement markings autonomously. Embodiments of the present invention discuss a method, a system, and a computer program for the determination and application of pavement markings for a paved area such as a road or parking lot, however, embodiments of the present invention are not limited to the determination of pavement markings for a road, but can also be used in the determination of markings for other surfaces such as athletic fields (e.g., a football field), a track, or other applicable non-paved area that may require painted markings.

Figure 1:
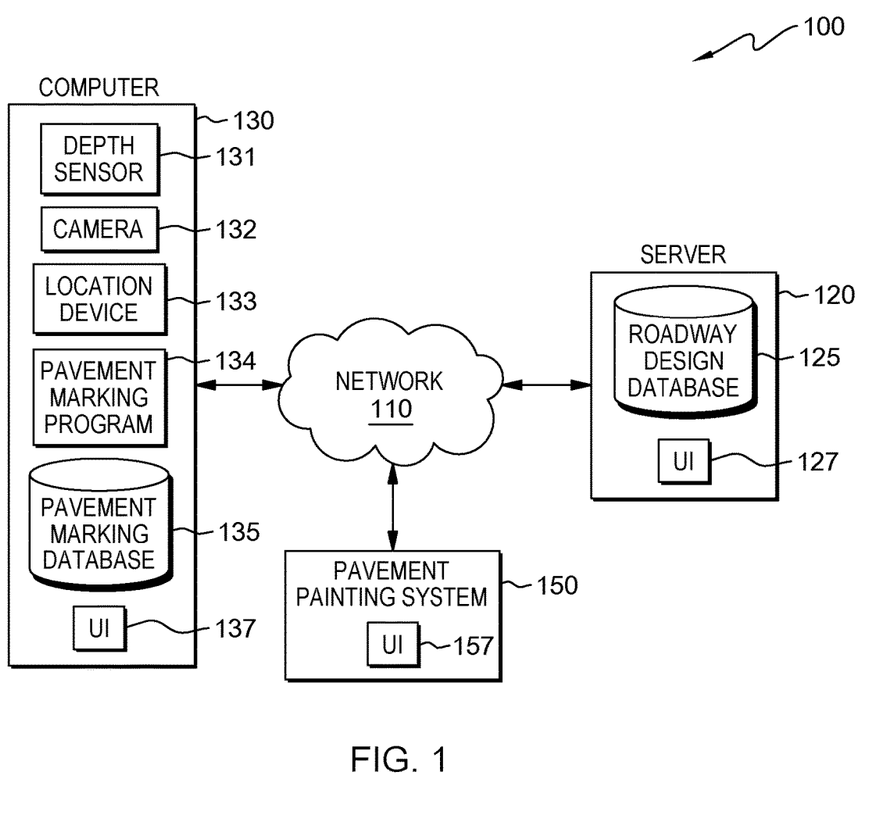
FIG. 1 is a functional block diagram illustrating a distributed data processing environment, in accordance with an embodiment of the present invention.

The present invention will now be described in detail with reference to the Figures. FIG. 1 is a functional block diagram illustrating a distributed data processing environment, generally designated 100, in accordance with one embodiment of the present invention.

FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes server 120, computer 130, and pavement painting system 150 connected through a network depicted as network 110. Network 110 can include wired, wireless, or fiber optic connections between server 120, computer 130, pavement painting system 150, and any computing devices not depicted but included in distributed data processing environment 100. Network 110 can be, for example, a local area network (LAN), a virtual LAN (VLAN), a wide area network (WAN), such as the Internet, a telecommunications network, or a combination of the these networks. Network 110 can include one or more virtual, wired, and/or wireless networks that are capable of receiving and transmitting data. In general, network 110 can be any combination of connections and protocols that will support communications between server 120, computer 130, pavement painting system 150, and other computing devices (not shown) within distributed data processing environment 100.

Server 120 can be a standalone computing device, a database server, a web server, a management server, a mobile computing device, a laptop computer, a desktop computer, or any other electronic device or computing system capable of receiving, sending, storing, and processing data. In various embodiments, each of the programs, applications, and databases on server 120 and computer 130 can reside on one or more other computing devices with distributed data processing environment 100, provided each have access to information and storage for implementation and operations of the present invention via network 110.

Server 120 includes roadway design database 125 and user interface (UI) 127. Server 120 may be a web server, a tablet computer, a netbook computer, a personal computer (PC), a personal digital assistant (PDA), a smart phone, or any programmable electronic device capable of communicating with computer 130, pavement painting system 150, and any other computing components and devices not shown in FIG. 1 in distributed data processing environment 100. Server 120 is capable of sending and receiving data such as road design plans to computer 130, pavement painting system 150, and other computing devices not depicted in FIG. 1 via network 110.

In various embodiments, server 120 sends road plans and data to computer 130, based on a user request or input to UI 127. Server 120 may receive data such as location data or photographs, or other information from computer 130 and pavement painting system 150 via network 110. A road plan can include information on required pavement markings, required signage, locations of various stations or points on a road (e.g., GPS location, survey location, or other locational data that may be available for road location and pavement marking), sets of digitized drawings, and other supporting information included in a road design. In some embodiments, pavement marking program 134 resides on server 120. In the depicted example, server 120 sends and receives data such as the location of a paint system and pavement markings to computer 130 and/or pavement painting system 150. In this example, server 120 may receive from computer 130 data from various sensors including sensors for determining a location, depth sensors, and cameras used to determine pavement markings for a current location. Server 120 may include internal and external hardware components, as depicted and described in further detail with respect to FIG. 3.

Roadway design database 125 resides on server 120 and stores road design plans used in road construction and road upgrades. Roadway design database 125 may receive, retrieve, and store information such as photographs, location data, and other information from computer 130, pavement painting system 150, and other computing devices not depicted in FIG. 1. In some embodiments, roadway design database 125 includes the painting details for creating pavement marks. For example, pavement marking size, shape, color, spacing, periodicity of repeating elements, type of paint, paint application thickness, or a document specifying the pavement marking requirements can be stored as data in roadway design database 125. While depicted on server 120, roadway design database 125 may be a separate database, may be on another computing device such as computer 130, or can reside on more than one other computing devices (e.g., a cloud) within distributed data processing environment 100, provided each has access to information and storage for implementation and operations of the present invention via network 110.

UI 127 is a user interface on server 120 providing an interface between a user of server 120 that enables a user of server 120 to interact with programs and data on server 120, computer 130, pavement painting system 150, and other computing devices (not shown). UI 127 may be a graphical user interface (GUI), an active area or line for text inputs, a web user interface (WUI), or other type of user interface and can display user options, application interfaces, and data including road designs and maps. In various embodiments, UI 127 receives user input via a touch screen, a keyboard, a mouse, a display, an audio, visual or motion sensing device, or another peripheral device. A user can use UI 127 to send road design information retrieved from roadway design database 125 to computer 130 or to send and receive and/or display other data sent from computer 130 and pavement painting system 150.

Computer 130 can be an augmented reality device, a laptop computer, a mobile computing device such as a smart phone, a wearable computer, a tablet computer, a notebook computer, a desktop computer, a server computer, or any other electronic device or computing system capable of receiving, sending, and processing data. Augmented reality is live direct or indirect view of a physical, real-world environment whose elements are augmented or enhanced by computer-generated input, for example, graphics, video, sound, or GPS data. As known to one skilled in the art, an augmented reality device can include hardware components such as a processor, a display, one or more sensors and input devices used to provide an augmented reality display or view such as an overlay of an element or an object on a real-world image on a display or in a displayed image. Some mobile computing devices like smartphones, tablet computers, smart glasses, and holographic goggles contain elements such as a camera, an accelerometer, a global position sensor, and a solid-state compass making them a suitable device for an augmented reality platform. Computer 130 is any programmable electronic device capable of communicating with server 120, pavement painting system 150, and other computing devices (not shown) within distributed data processing environment 100 via network 110 that can determine a location, a paved area size, a pavement environment, and pavement markings.

In various embodiments, computer 130 includes depth sensor 131, camera 132, location device 133, pavement marking program 134, pavement marking database 135, and UI 137. In some embodiments, computer 130 includes one type of device (e.g., one of a camera or a depth sensor) to provide the capabilities such as a determination of the presence of an existing pavement mark and the distance to objects provided by depth sensor 131 and camera 132. For example, computer 130 may include one or more cameras (e.g., one or more of camera 132) but not depth sensor 131. In this example, computer 130 can analyze photographs or digital images captured by one or more cameras to determine a road width, a road environment, pavement marking location, and pavement marking quality (e.g., fading or wear) using one or more of known digital image analysis software algorithms (e.g., image contrast, color contrast, color intensity, shape matching, etc.).

In various embodiments, computer 130 is integrated with pavement painting system 150. For example, computer 130 may be mounted on pavement painting system 150 or be integrated into pavement painting system 150. For example, computer 130 and pavement painting system 150 may share hardware such as physical hardware (e.g., a frame or chassis, a paint dispersion or application system, a display, etc.), electrical elements (e.g., sensors, GPS or location devices, camera, etc.), computer components, or software. In various embodiments, when computer 130 includes pavement painting system 150, the display or user interface (e.g., one of UI 137 or UI 157) for the combined system provides capability for augmented reality such as an overlay of pavement markings for paint application depicted on a real-time view of the paved surface.

In other embodiments, a vehicle that is an automated, robotic painting system such as an autonomous or a self-driving car, kart, or a drone that integrates the various hardware components, sensors, and software of computer 130 and pavement painting system 150. For example, an automated, robotic painting system using pavement marking program 134 can determine if one or more pavement markings are required at a location determined by the system and can automatically apply the pavement markings using paint application equipment on the automated, robotic painting system.

In some embodiments, computer 130 is a mobile computing device or computer on a drone, an aerostat, or a hybrid aerostat capable of sending pavement-marking data to pavement painting system 150. Aerostats or hybrid aerostats commonly used for aerial surveys, surveillance, or aerial photography can be an aircraft the remains aloft primarily using aerostatic buoyancy (e.g., a tethered balloon). A hybrid aerostat that uses both static buoyancy and dynamic airflow as provided by a propulsive power (e.g., an engine) or tethering in the wind (e.g., like a kite or an Allsopp Helikite®) that are more stationary and lower cost than a drone or unmanned aerial vehicle (UAV). In this example, computer 130 is an aerial mobile computing device capable of performing the functions discussed above to determine the pavement markings for a location and provide pavement marking data for a current location to pavement painting system 150.

Computer 130 connects to server 120 and pavement painting system 150 via network 110. In various embodiments, computer 130 sends and receives data such as pavement markings, a pavement marking specification (e.g., MUTCD), and road plans which may include digital design data in a tagged image file format (TIFF) or a station (e.g., a defined location from a survey) to and from server 120 and pavement painting system 150. Computer 130 stores data such as a road plan in a database, for example as pavement marking database 135. In some embodiments, computer 130 retrieves data such as a road specification from a database such as roadway design database 125 on server 120, or another storage location (not shown) within distributed data processing environment 100. Computer 130 may include internal and external hardware components, as depicted and described in further detail with respect to FIG. 3.

Depth sensor 131 is composed of one or more depth detection sensors. Depth sensor 131 provides data such as distance to elements on a road or objects around the road. In various embodiments, depth sensor 131 sends the measured distances to pavement marking program 134 and may be used to determine a road layout. For example, the road layout can include distances such as a distance to one or more edges of a paved area used for determining a road width, the distance to objects such as sidewalks, curbs, reflectors, drainage grates, roadway signs in the vicinity of the road or paved area, and other obstacles or elements such as tree branches or railway crossings on or in the vicinity (e.g., three to four meters) of a road or paved area.

In some embodiments, depth sensor 131 is used for elements or landmarks within the field of vision at a location. In an embodiment, a range used for a depth sensor 131 is based on a level of accuracy of the one or more sensors used in computer 130. For example, ranges that may be used with depth sensor 131 include the range of a sensor such as depth sensor 131 can be determined based on the sensor accuracy. For example, a range over which depth sensor 131 provides an accuracy of one to ten centimeters for objects or elements around a paved area and an accuracy of one tenth of a centimeter to ten centimeters for pavement markings.

In various embodiments, depth sensor 131 uses hardware and software algorithms from depth detection technologies known to one skilled in the art. For example, depth sensor 131 can use three dimensional (3D) scanners, range imaging cameras including time-of-flight cameras, structured light 3D scanners, stereographic triangulation cameras or range imagers, laser range finders, and any other suitable depth detection technologies used in sensors to determine a distance to an element on a paved area, or in the vicinity of a paved area such as a road. In various embodiments, one or more depth sensors 131 are included in computer 130. Depth sensor 131 sends data, such as the distance from a pavement edge to a pavement edge (e.g., for a road width), to pavement marking program 134, pavement marking database 135, or another database on computer 130 or server 120 for storage.

Camera 132 provides the ability to capture photographs or digital images of a paved area and the paved area surroundings (e.g., a road and the road surroundings). While FIG. 1 depicts computer 130 with a camera for camera 132, in various embodiments, computer 130 includes one or more cameras. In some embodiments, the recorded digital images are videos or still digital images extracted from video digital image files. The recorded digital images can be used by pavement marking program 134 to determine the presence of pavement markings, the quality of existing pavement markings, the location of existing pavement markings, and can be used to verify or provide additional information on computer 130's current location (e.g., based on landmarks, survey pins, or other visual location indicators). In some embodiments, pavement marking program 134 uses the digital images provided by camera 132 to determine a distance to one or more objects such as a road edge or stop sign. For example, pavement marking program 134 may use one or more known software algorithms to determine distance from digital images captured by one or more cameras for camera 132 (e.g., camera 132 can be used to provide distances instead of or in addition to depth sensor 131). In various embodiments, camera 132 sends one or more captured digital images to pavement marking program 134 and pavement marking database 135.

Figure 3:
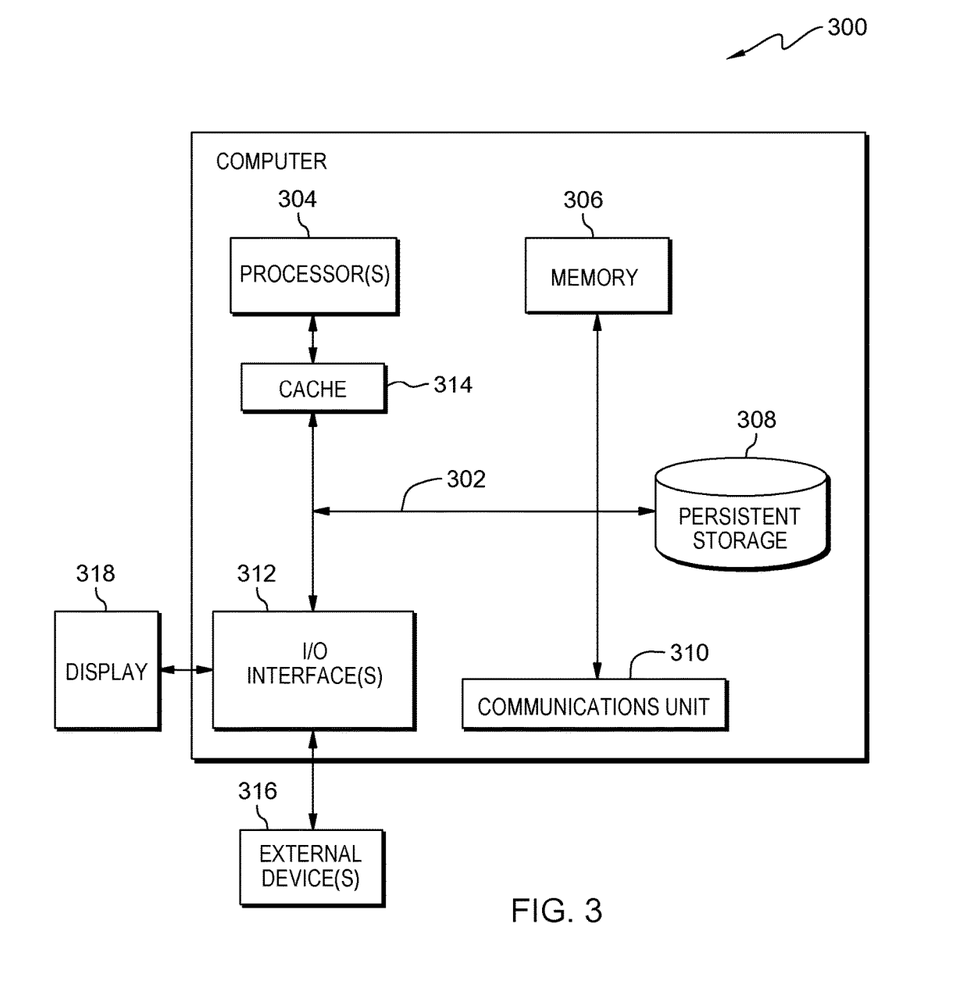
FIG. 3 depicts a block diagram of components of a computer, in accordance with an illustrative embodiment of the present invention.

Location device 133 provides a location of computer 130. Location device 133 uses one or more known technologies that can provide a location accurate (e.g., within 0.5 to twenty cm) for computer 130. In various embodiments, location device 133 is a high precision global positioning system (GPS). In some embodiments, location device is one or more of a local positioning system (e.g., based off a known cell tower location, etc.), theodolite based software or software application, or any other suitable location device technology. In various embodiments, location device 133 is a sensor. Location device 133 sends data such as a current location to pavement marking program 134 and to pavement marking database 135. In one embodiment, location device 133 sends data such as a current location to persistent storage 308 in computer 130.

Pavement marking program 134 receives a current location from a location sensor (e.g., location device 133). In various embodiments, pavement marking program 134 determines if pavement markings exist on a road at the current location. In various embodiments, pavement marking program 134 determines if no pavement markings exist (e.g., on a new road surface), if the existing pavement markings are acceptable (e.g., no painting required), if the existing pavement markings should be refreshed or re-painted, or if the existing pavement markings are off location and should be erased and re-applied in the proper location. In various embodiments, when pavement marking program 134 determines the pavement or road needs pavement marking, pavement marking program 134 retrieves one or more pavement markings identified in the road plans for the current location from a database such as pavement marking database 135 or roadway design database 125. In some embodiments, pavement marking program 134 determines markings for a location on another surface. For example, line marks and field marking for a football field on a turf or a grass surface. In various embodiments, pavement marking program 134 retrieves pavement marking specifications (e.g., MUTCD) from a database (e.g., pavement marking database 135, roadway design database 125 on server 120, or another database on a computer in distributed data processing environment 100). In an embodiment, pavement marking program 134 uses pavement markings that are included in the road plans. For example, pavement marking program 134 retrieves the pavement marking data detailing the shape, size, spacing, and location of the pavement markings from the road plan rather than retrieving the pavement marking specification stored in pavement marking database 135.

Pavement marking program 134 receives a current location from location device 133 and receives distances from depth sensor 131 associated with the road at the current location (e.g., a distance to one or more road edges to determine a road width and a road center, distance to curb, distance to an on-ramp, distance to an intersection, etc.). Additionally, pavement marking program 134 receives digital images or photographic data of the road surface and the surrounding road area including possible existing pavement markings and signage from camera 132. In various embodiments, pavement marking program 134 resides on computer 130. In some embodiments, pavement marking program 134 resides on another computer such as server 120 sending and receiving data such as sensor data and pavement marking data to and from pavement painting system 150, sensors (e.g., location device 133, depth sensor 131, and camera 132), and databases such as roadway design database 125 on server 120.

Pavement marking program 134 analyzes the road plan and received data from depth sensor 131, camera 132, and location device 133 to determine the location and type of pavement markings for application on a road by pavement painting system 150. Pavement marking program 134 determines from one or more of digital image data or depth sensor data if there are existing pavement markings or lines and determines if the existing pavement markings meet a number of pre-determined thresholds for pavement marking quality.

In various embodiments, pavement marking program 134 provides the pavement marking data to pavement painting system 150 for pavement marking application. In various embodiments, pavement marking program 134 sends data for pavement marking application to an augmented reality display in pavement painting system 150. For example, the display provides an overlay of pavement markings on a real-time view of a road to a user with a manual pavement painting system for pavement painting system 150 using a handheld or mounted display (e.g., a smart phone with an augmented reality overlay depicting a pavement marking location). In another embodiment, pavement marking program 134 provides data for pavement marking to a painting system in an automated robotic vehicle or a drone.

In various embodiments, pavement marking database 135 stores pavement marking details (e.g., a pavement marking specification in MUTCD) and one or more road plans. Pavement marking details may include digital design data in a tagged image file format (TIFF) or any other digital design data format that may be utilized by pavement painting system 150 to paint markings such as lines, arrows, words, or other pavement markings for traffic control or pedestrian directions on a road or paved surface. Pavement marking program 134 retrieves required data such as pavement marking specifications, pavement design, and paint application related data for one or more pavement markings identified in a road plan for a current location from pavement marking database 135 to send to pavement painting system 150. While depicted on computer 130, in some embodiments, pavement marking database 135 is on another computer, is a standalone database, or is included on one or more computers or computing devices (e.g., resides on a cloud computing environment).

UI 137 is a user interface on computer 130 providing an interface between a user of computer 130 that enables a user of computer 130 to interact with programs and data on server 120, pavement painting system 150, and other computing devices (not shown). UI 137 may be a graphical user interface (GUI), an active area or line for text inputs, a web user interface (WUI), a heads-up display (HUD), or other type of user interface and can display user options, application interfaces, data including maps, digital images from camera 132, pavement markings, overlays of pavement markings projected on a real-time image, and includes displaying any other information that a program or application may present to a user. As known to one skilled in the art, a heads-up display (HUD) is any transparent display that presents data without requiring a user to look away from their standard viewpoint (e.g., see data while looking forward as can be done with holographic goggles or smart-glasses).

In an embodiment, UI 137 uses a virtual retinal display. A virtual retinal display is a display scanned directly on a user's retina that appears to be floating in space in front of the user. In some embodiments, computer 130 and pavement painting system 150 are coupled to form a single unit. In this case, when computer 130 and pavement painting system 150 are integrated, UI 137 is an augmented reality display. For example, UI 137 may be a hand held display such as a smart phone displaying an overlay of pavement markings on a real-time image of a road. In some embodiments, UI 137 is used to by a user to send painting instructions to pavement painting system 150 for pavement marking.

In various embodiments, pavement painting system 150 applies pavement markings to a road or other paved surface. In various embodiments, pavement painting system 150 is any known painting system for pavement painting used in road construction or road repair. In some embodiments, pavement painting system 150 includes computer 130. For example, computer 130 is mounted on pavement painting system 150 or integrated into a dashboard of pavement painting system 150. In other embodiments, pavement painting system 150 is in an automated, robotic system (i.e., a self-driving car or other self-driving vehicle with a painting system and computing capability) or a drone integrating the functions and elements of computer 130 and the ability to apply pavement markings in one unit or vehicle.

In some embodiments, pavement painting system 150 includes a location device 133. For example, location device 133 in pavement painting system 150 can be used to correlate pavement marking data for a current location of computer 130 to a current location for pavement painting system 150. In one embodiment, when pavement painting system 150 is a vehicular, automated, robotic painting system where the automated, robotic painting system is capable of being programmed to place traffic cones before painting and to remove or pick-up traffic cones after road painting is complete.

In some embodiments, pavement painting system 150 includes UI 157. In various embodiments, UI 157 is a display capable of providing an overlay using augmented reality technology. In one embodiment, UI 157 uses spatial augmented reality such as digital projectors to display information on a physical object such as a pavement marking projected on a road surface. In this case, the projection from UI 157 can be used as a visual guide to an operator of pavement painting system 150 for applying pavement markings to the correct location. In various embodiments, UI 157 receives a user input via a touch screen, a key board, a mouse, a display, an audio, visual or motion sensing device or other peripheral device standard in computer devices. In various embodiments, UI 157 includes the capability to provide an augmented reality such as an overlay of determined pavement markings on a real-time view of a road or paved area.

Figure 2:
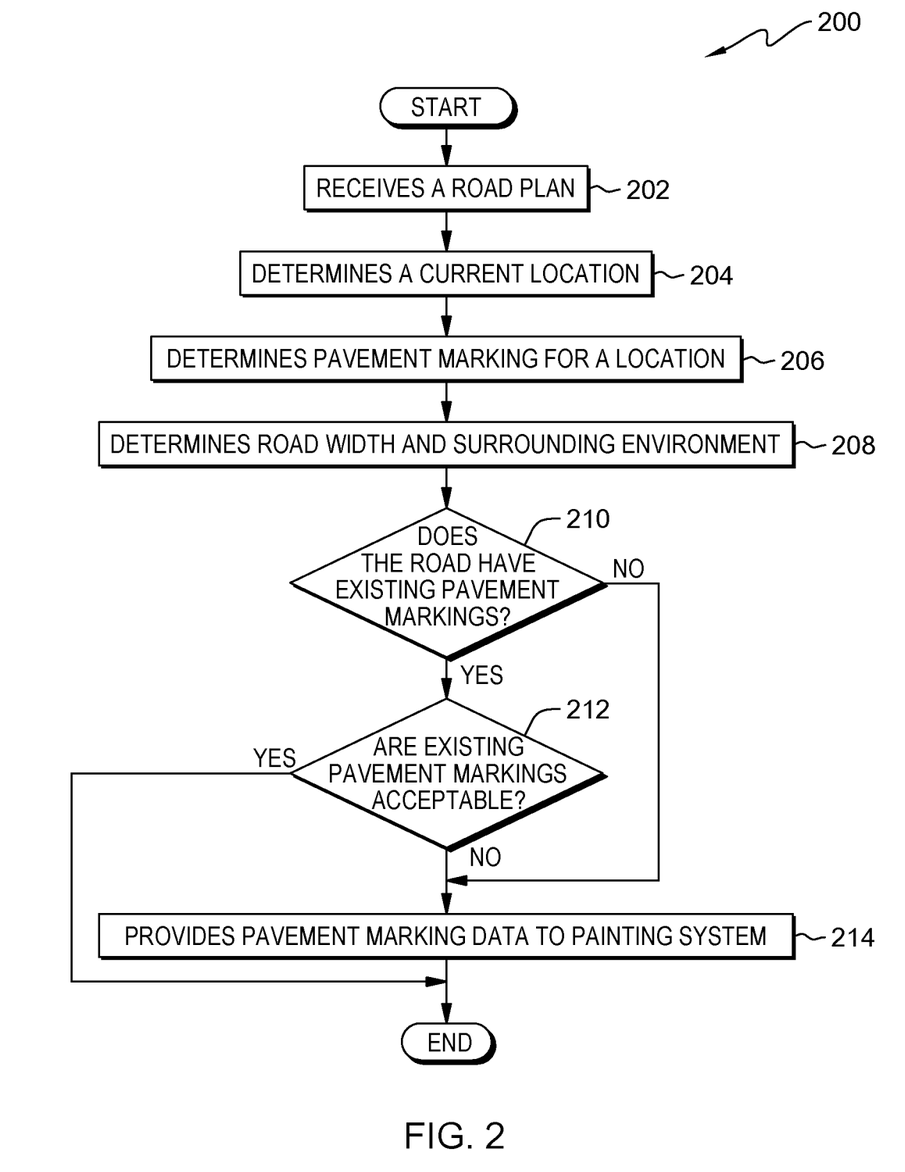
FIG. 2 is a flowchart depicting operational steps of the pavement marking program of FIG. 1, for determining a pavement marking for a paved area, in accordance with an embodiment of the present invention.

FIG. 2 is a flowchart 200 depicting operational steps for pavement marking program 134 for determining the pavement marking for a paved area, in accordance with an embodiment of the present invention. In step 202, pavement marking program 134 receives a road plan which may be a parking lot plan or soccer field layout from server 120. In various embodiments, based on a user input to UI 127, server 120 retrieves a plan from roadway design database 125 to send to computer 130. In some embodiments, computer 130 receives a road plan from one or more other computing devices (not shown) in distributed data processing environment 100. Pavement marking program 134 can receive a road plan that includes a plan of record design for the road. The plan of record design for the road includes one or more of digitized road drawings for the road design, maps, surveys, areal maps, station positions, road location points, distances to surveying pins, station points, or significant landmarks, precision GPS locations, signage, and assigned pavement markings for the road at the current location (e.g., location on the road such as identified by high precision GPS data, survey data, or other similar location data).

In step 204, pavement marking program 134 determines a current location. Using location device 133, pavement marking program 134 determines a current location for computer 130. In some embodiments, for example in embodiments where pavement painting system 150 is coupled to computer 130, pavement painting system 150 includes a location device, such as location device 133 used to transmit a location of pavement painting system 150 to pavement marking program 134. In other embodiments, a location for pavement painting system 150 is determined by pavement marking program 134 using a current location for computer 130 combined with a distance and/or a location determined based on data provided depth sensor 131 or camera 132. In various embodiments, location device 133 may use high precision GPS to identify the current location for computer 130. In some embodiments, pavement marking program 134 uses a location technology that matches one or more of the location data types supplied in the road plan. For example, pavement marking program 134 may use a theodolite software application for location device 133 to match theodolite data (e.g., from a survey of the road area) included in a road plan. A theodolite is a precision instrument for measuring angles commonly used in surveying applications.

In step 206, pavement marking program 134 determines pavement markings for a location. Using the determined current location, pavement marking program 134 identifies from the road plan the assigned pavement markings for the location. For example, pavement marking program 134 analyzes the road plan and determines the assigned pavement markings identified in the road plan for the current location. In various embodiments, pavement marking program 134 retrieves from pavement marking database 135 the identified pavement markings determined from the road plan for the current location.

The retrieved pavement marking from pavement marking database 135 includes data, detail, and specifications for painting the identified and retrieved pavement markings. The retrieved pavement painting data includes information on pavement marking shape, size, location, periodicity, proximity to associated markings and road signage, and may also include a required paint thickness and paint type. Pavement marking data and details may be specified by one of a local, a state, a province, or a federal regulation such as a traffic regulatory body or department, or in some cases, by a designer or an engineer for the road design. For example, pavement markings may be specified in a department of transportation document or manual such as the MUTCD. In some embodiments, pavement marking program 134 retrieves pavement markings from one of roadway design database 125 on server 120 or the received road plan.

In step 208, using depth sensor 131, pavement marking program 134 determines a road center and the surrounding environment. Pavement marking program 134 makes a determination of a road width and a location of the center of the center of the road using the distance to the road edges measured by depth sensor 131. Depth sensor 131 may use three dimensional (3D) scanning technology or time-of-flight technology (e.g., time-of-flight camera or sensors) to determine one or more of the following: the distance to the road edges, a road width, a distance to a curb, a distance to a side walk, a sign, a cross-walk, an on-ramp, a landmark, a survey mark based station, a survey pin, or a distance to any other significant objects in the vicinity of the pavement or road.

In some embodiments, pavement marking program 134 uses depth sensor 131 to determine the distances to elements directly connected to a paved area. For example, a distance to a road edge, to a curb, to an intersection, to an on-ramp, or a distance to a pavement marking such as a line when depth sensor 131 can detect a change in road surface texture or color. In other embodiments, pavement marking program 134 uses depth sensor 131 to determine objects and elements outside of a paved area. For example, pavement marking program 134 uses depth sensor 131 to determine a distance to elements or objects such as signs, survey pins, or sidewalks beyond a paved area where the range of distance beyond the pavement that are limited by the desired accuracy of depth sensor 131 (e.g., a distance range with an accuracy of two centimeters).

In various embodiments, pavement marking program 134 determines the location of the pavement markings based, at least in part, on the center of the road. For example, depth sensor 131 sends a distance for each pavement edge to pavement marking program 134 to determine a road width, a location for the center of the road, and pavement marking program 134 determines a distance to a curb or a bike lane with respect to the center of the road. In some embodiments, pavement marking program 134 receives one or more digital images from camera 132 used by pavement marking program 134 to determine the center of the road for pavement painting.

In decision step 210, pavement marking program 134 determines if the road has existing pavement markings. In various embodiments, pavement marking program 134 receives digital images from camera 132 of the road or pavement surface that are used for an evaluation of the presence of existing pavement markings. In one embodiment, depth sensor 131 provides information and data on the details of the road surface (e.g., variations in surface indicating a layer of paint on the surface or a variation of surface color such as a variation between a pavement color and a pavement marking color, or a level of contrast in reflected light intensity indicating the presence of pavement markings) to determine if existing pavement marks are present. Pavement marking program 134 uses known digital image analysis techniques and software algorithms (e.g., a road surface color contrast analysis or a surface texture analysis using digital image data) on the received digital images from camera 132 to determine if pavement markings are present on the road surface.

If no existing pavement markings are identified (no branch of decision 210), then pavement marking program 134 provides pavement marking data to pavement painting system 150 (step 214). For example, pavement marking program 134 provides to pavement painting system 150 the retrieved details for painting the pavement markings retrieved in step 206. Pavement marking program 134 retrieves the pavement marking data for the current location identified in step 206 and sends the pavement marking data to pavement painting system 150. In this case, pavement marking program 134 sends pavement marking or painting data to pavement painting system 150. The pavement marking data is for painting the identified pavement markings for the current location. Using the provided pavement marking data from pavement marking program 134, pavement painting system 150 can apply lines and other identified pavement markings on a new road surface (e.g., a new road or re-paved road without any pavement markings).

In various embodiments, pavement marking program 134 outputs pavement marking data using augmented reality technology such as an overlay of one or more pavement markings projected on a real-world road image of the road or paved area in UI 137. For example, as previously discussed, pavement painting system 150 may display on a laptop or a handheld smart phone an overlay of pavement markings for the current location. In another example as previously discussed, computer 130 may be an augmented reality device such as smart glasses or goggles. In one embodiment, pavement marking program 134 is integrated into an automated, robotic system or vehicle and outputs directly to a painting system in the robotic vehicle.

In some embodiments, if pavement marking program 134 determines that existing pavement markings are present upon analysis of the digital images of the road captured by camera 132 (yes branch of decision 210), then pavement marking program 134 evaluates if the existing pavement markings are acceptable (decision step 212). Pavement marking program 134 uses a set of thresholds to determine if pavement markings meet one or more pre-determined threshold for an acceptable pavement mark quality for the existing pavement markings. In various embodiments, pavement marking program 134 utilizes pre-determined thresholds from a pavement marking specification (e.g., MUTCD) for at least a part of the determination of acceptability of existing pavement marking quality. For example, pavement marking program 134 can determine if the current existing pavement marking is within a pre-determined or specified threshold distance to a desired location. In this example, a threshold can be that an acceptable existing pavement mark is within a range of plus or minus ten centimeters from the desired location of the pavement mark as depicted in the road plan. In another threshold example, the existing pavement marking should cover at least ninety percent of the pavement mark area (e.g., no more than ten percent of a pavement marking missing in a square foot of pavement) as determined from the specified pavement mark to be acceptable (e.g., no large missing or worn off areas of paint). In this example, pavement marking program 134 compares the size and shape of the pavement mark of a specified pavement mark in the road plan retrieved in step 206 to the existing pavement mark. Another example of a pavement marking threshold for an existing pavement mark can be a required level of contrast between an existing mark and the pavement. For example, a required level of brightness or a level of color saturation for a pavement marking may be required for an acceptable existing pavement mark (e.g., a yellow marking must be at a forty percent saturation level). In another example, a pavement marking threshold can be a specified color for the pavement mark (e.g., a turn arrow must be yellow).

For each pavement marking depicted in the digital image data, when pavement marking program 134 evaluates that the existing pavement marking is acceptable (yes branch decision 212), then, no re-painting of the existing pavement markings in the current location is needed. When each of the pavement markings in the provided digital image data are evaluated by pavement marking program 134, the program may end. Pavement marking program 134 does not send pavement marking data to pavement painting system 150 when the existing pavement markings meet the pre-determined thresholds for acceptable quality. In various embodiments, when pavement marking program 134 determines that the existing pavement markings are acceptable at a location, computer 130 is moved to a new location and pavement marking program 134 determines a new current location and evaluates the pavement markings for the new location. In this example, pavement marking program 134 repeats as required the steps 202 to 214.

When pavement marking program 134 determines that the existing pavement markings are not acceptable (no branch of decision 212), then pavement marking program 134 provides pavement marking data to pavement painting system 150 (step 214). When the existing pavement markings do not meet the specified or pre-determined quality levels or thresholds, pavement marking program 134 determines that the pavement marking should be re-applied. In some cases, when the existing pavement marks do not meet expected pavement location thresholds as provided in a pavement specification such as MUTCD or other pavement marking specification configured as a pre-set threshold in pavement marking program 134 then, pavement marking program 134 determines that the existing pavement marks should be removed and re-applied at the correct location.

In some embodiments, when pavement marking program 134 provides pavement marking data to pavement painting system 150, where pavement painting system 150 is a manual paint system. In this example, the pavement markings determined by pavement marking program 134 may be displayed as an augmented reality overlay on a real-time display of the pavement in a hand held device such as a smart phone. In another example, as the pavement markings can be added as an overlay on a displayed static digital image or video of the paved area in a current location shown on a mounted display, UI 157 on manual pavement painting system 150. In some embodiments, pavement marking program 134 sends pavement marking data to an augmented reality display in smart glasses worn by the operator of the manual painting system.

In some embodiments, pavement marking program 134 includes an overlay of the pavement marking in smart glasses worn by an operator of a vehicular painting system (e.g., pavement painting system 150). In various embodiments, computer 130 is mounted or integrated in a manually operated vehicular pavement painting system 150. In this example, pavement markings are displayed as an augmented reality overlay on one of UI 137 or UI 157. In one embodiment, pavement marking program 134 provides pavement marking data to pavement painting system 150 for projection on the road surface indicating the location for paint application by a driver or paint system operator. In another embodiment, the functions and hardware of computer 130 and pavement painting system 150 are combined in an automated robotic paint system that includes a mobile painting system with the sensors, cameras, and software to determine pavement markings for a location and automatically guide the robotic vehicle during paint application. In this example, pavement marking program 134 includes additional software algorithms known to one skilled in the art to determine a path for the automated robotic paint system based on location device 133 data, depth sensor 131 data, and camera 132 digital image data. Upon completion of pavement marking application by pavement painting system 150, computer 130 and pavement painting system 150 can be moved to another location and an evaluation of pavement markings for the new location can be performed by pavement marking program 134 (e.g., steps 202 to 214 are repeated as needed for the new location).

FIG. 3 depicts block diagram 300 of components of computer 130 in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Computer 130 includes communications fabric 302, which provides communications between cache 314, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses or a crossbar switch.

Memory 306 and persistent storage 308 are computer readable storage media. In this embodiment, memory 306 includes random access memory (RAM). In general, memory 306 can include any suitable volatile or non-volatile computer readable storage media. Cache 314 is a fast memory that enhances the performance of computer processor(s) 305 by holding recently accessed data, and data near accessed data, from memory 306.

Programs and data used for implementation of embodiments of the present invention, i.e., pavement marking program 134 may be stored in persistent storage 308 and in memory 306 for execution by one or more of the respective computer processors 304 via cache 314. In an embodiment, persistent storage 308 includes a magnetic hard disk drive. Alternatively, or in addition to a magnetic hard disk drive, persistent storage 308 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices. In these examples, communications unit 310 includes one or more network interface cards. Communications unit 310 may provide communications through the use of either or both physical and wireless communications links. Pavement marking program 134 may be downloaded to persistent storage 308 through communications unit 310.

I/O interface(s) 312 allows for input and output of data with other devices that may be connected to computer 130. For example, I/O interface 312 may provide a connection to external devices 316 such as a keyboard, keypad, a touch screen, and/or some other suitable input device. External devices 316 can also include portable computer readable storage media such as, for example, thumb drives, portable optical or magnetic disks, and memory cards. Software and data used to practice embodiments of the present invention can be stored on such portable computer readable storage media and can be loaded onto persistent storage 308 via I/O interface(s) 312. I/O interface(s) 312 also connect to a display 318.

Display 318 provides a mechanism to display data to a user and may be, for example, a computer monitor or an augmented reality display such as smart glasses.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application, or technical improvement over technologies found in the marketplace, or to enable others of ordinary skill in the art to understand the embodiments disclosed herein.

What is claimed is:

1. A method for determining and applying pavement markings, the method comprising:

determining, by one or more computers, a location of a first computing device based on data received from one or more location devices associated with the first computing device, wherein at least one of the one or more location devices includes at least data from a precision global positioning system, and wherein the first computing device is an automated robotic painting system that is one of an autonomous car, an autonomous kart, or an autonomous drone;

retrieving, by one or more computers, pavement marking data for one or more pavement markings for the location;

determining, by one or more computers, whether one or more existing pavement markings are present at the location, wherein the determining includes determining, based, at least in part, on at least one of: a digital image received from one or more cameras and sensor data received from one or more sensors;

responsive to determining that one or more existing pavement markings are present at the location, determining, by one or more computers, whether each of the one or more existing pavement markings meet one or more pre-determined thresholds for an acceptable pavement marking quality, wherein the one or more pre-determined thresholds for the acceptable pavement marking quality level include at least one of: a level of contrast between a pavement marking color and a pavement color, a percent of a pavement marking present, a location of the pavement marking as compared to a specified pavement mark for the location of an existing pavement marking, and any other threshold of the one or more pre-determined thresholds for an acceptable quality level included in a governing traffic regulation document;

responsive to determining each of the one or more existing pavement markings do not meet the one or more pre-determined thresholds for an acceptable pavement marking quality level, providing, by one or more computers, pavement marking data, wherein providing pavement marking data includes providing data for removal of one or more of the one or more existing pavement markings and providing pavement marking data for display on the first computing device using spatial augmented reality; and applying, by the first computing device, one or more lines and other identified pavement markings, based, at least in part, on the provided pavement marking data.

* * * * *